(12) United States Patent
Latza

(10) Patent No.: US 7,182,865 B2
(45) Date of Patent: Feb. 27, 2007

(54) DEVICE FOR SEPARATING WHOLE BLOOD UNDER GRAVITATIONAL FORCE

(76) Inventor: Sibylle Latza, Bluecherstrasse 47, 66386 St. Ingbert (DE)

( * ) Notice: Subject to any disclaimer, the term of this patent is extended or adjusted under 35 U.S.C. 154(b) by 0 days.

(21) Appl. No.: 11/143,560

(22) Filed: Jun. 2, 2005

(65) Prior Publication Data

US 2006/0011545 A1 Jan. 19, 2006

Related U.S. Application Data

(63) Continuation of application No. PCT/EP03/13705, filed on Dec. 4, 2003.

(30) Foreign Application Priority Data

Dec. 4, 2002 (DE) .................................. 102 56 848

(51) Int. Cl.
*B01D 63/00* (2006.01)

(52) U.S. Cl. .............. 210/257.2; 210/257.1; 210/321.6; 210/435; 210/650; 210/651; 604/6.02; 604/6.03; 604/6.09; 604/6.1; 604/6.15; 604/7; 604/9

(58) Field of Classification Search ............ 210/252, 210/257.1, 257.2, 258, 321.6, 321.65, 435, 210/650, 651; 604/4.01, 5.01, 6.02, 6.03, 604/6.04, 6.09, 6.1, 6.11, 6.15, 7, 9
See application file for complete search history.

(56) References Cited

U.S. PATENT DOCUMENTS

| 4,639,243 A | 1/1987 | Schmidt et al. |
| 4,898,573 A * | 2/1990 | Takenaka et al. ........... 604/6.04 |
| 4,964,847 A | 10/1990 | Prince |
| 5,527,472 A | 6/1996 | Bellotti et al. .............. 210/767 |
| 5,858,238 A * | 1/1999 | McRea et al. .............. 210/645 |
| 7,025,881 B2 * | 4/2006 | Heim ....................... 210/257.2 |
| 2002/0183678 A1 | 12/2002 | Heim ........................ 604/6.04 |
| 2005/0263452 A1* | 12/2005 | Jacobson .................... 210/484 |

FOREIGN PATENT DOCUMENTS

| DE | 33 02 383 A1 | 7/1984 |
| DE | 295 16 471 U1 | 3/1996 |
| EP | 266 683 A2 | 5/1988 |
| EP | 349 188 B1 | 1/1990 |
| WO | WO 02/13888 A1 | 2/2002 |

OTHER PUBLICATIONS

International Search Report in PCT/EP2003/013705 dated Jun. 15, 2004.
International Preliminary Examination Report in PCT/EP2003/013705 dated Sep. 29, 2004.

* cited by examiner

*Primary Examiner*—John Kim
(74) *Attorney, Agent, or Firm*—Marshall, Gerstein & Borun LLP

(57) ABSTRACT

Method for separating whole blood into a leukocyte-depleted erythrocyte concentrate and thrombocyte-containing plasma, in which method whole blood is separated in a first step into an erythrocyte concentrate and plasma in a plasma filter and is then separated into a second erythrocyte concentrate and more thrombocyte-containing plasma during the return flow through the same plasma filter, the erythrocyte concentrate obtained being mixed with an additive solution, and the entire separation system being closed on itself and sterile.

6 Claims, 4 Drawing Sheets

1.)   2.)   3.)

DEVICE FOR SEPARATING WHOLE BLOOD UNDER GRAVITATIONAL FORCE

CROSS-REFERENCE TO RELATED APPLICATION

This is a continuation of International Application No. PCT/EP2003/013705 filed Dec. 4, 2003, the entire disclosure of which is hereby incorporated herein by reference.

BACKGROUND OF THE INVENTION

1. Field of the Invention

The invention relates to a method for separating whole blood into a leukocyte-depleted erythrocyte concentrate and plasma, and to a device for carrying out this method.

2. Related Technology

In whole-blood separation, whole blood taken from blood donors is separated into the individual blood components. These are principally erythrocyte concentrates or plasma fractions which may be cell-free or contain thrombocytes.

Separation of whole blood nowadays either involves use of specially designed production areas, high-performance centrifuges, blood separation appliances such as plasma filters, and specially trained personnel, or plasma separators are employed for direct recovery of individual or combined blood components.

As a result of the increased quality requirements and the legal regulations, and in view of the high-performance blood separators which have been developed in the meantime, it has become virtually impossible for a transfusion specialist or for quite small hospitals to produce blood products in this way and to sell blood products produced in this way. It would therefore be useful to permit simple separation of blood components in this sector too, without compromising the high quality standards. It would also be useful to be able to produce such blood products on this basis without high investment in technology and thus without excessive costs.

DE 33 02 383 A1 discloses a method and a device for recovering blood plasma in which in vivo whole blood is taken from a patient and is then divided into an erythrocyte concentrate and a plasma fraction in a plasma filter.

In a further configuration, the erythrocyte concentrate is returned to the patient through the plasma filter with renewed separation of a further plasma fraction.

Although double fractionation of plasma is performed here, the erythrocyte concentrate is returned to the blood donor again directly without interim storage.

EP 349 188 describes a method for separating blood into blood components, and a separator unit for recovering these blood components. According to this method, blood is first conveyed from a whole-blood container through a filter which removes leukocytes and also blood platelets. The filtered blood is then collected in a primary bag which is then subjected to centrifugation to divide the blood up into a plasma fraction and an erythrocyte concentrate. The plasma is conveyed through a plasma line into a further plasma bag.

As has already been explained above, this method is technically complex because of the use of a centrifuge. Moreover, the plasma cannot be separated completely, because there may otherwise be a danger of mixing with erythrocytes.

U.S. Pat. No. 5,527,472 likewise describes a closed system for separation of whole-blood constituents by means of centrifugation. In this method, the centrifugation initially takes place in a first bag with division into plasma and an erythrocyte concentrate, to which a substitute solution is then mixed. This mixture is then freed of leukocytes in a leukocyte-removing filter, so that an erythrocyte concentrate with substitute solution is obtained, but which still contains a high proportion of plasma.

This method too is technically complex, and a high proportion of blood plasma remains in the erythrocyte concentrate.

WO 02/13888 discloses a filter arrangement for separating blood into plasma and cellular components using filter type Mikro PSE-TF 10 from Akzo Faser AG. The arrangement is closed off airtight and impervious to microbes. Before separation of the whole blood, leukocytes and thrombocytes are separated off, if appropriate. By reversing the direction of flow through the filter arrangement after the first pass, a hematocrit value of at least 80 can be obtained in the erythrocyte fraction.

WO 02/13888 does not disclose simultaneous separation of whole blood into an erythrocyte concentrate and a thrombocyte-containing plasma.

As a result of this, the object of the invention is to provide a technically simple method for separation of whole blood into an erythrocyte concentrate and a thrombocyte-containing plasma, in which as little plasma as possible remains in erythrocyte concentrate, and which method can be performed directly at the donor site, in particular without any delay after withdrawal.

GENERAL DESCRIPTION OF THE INVENTION

Accordingly, the invention provides a method for separating whole blood under gravitational force, the method including the steps of:
  a) separating whole blood into a first erythrocyte concentrate and into a first thrombocyte-containing plasma fraction by filtration, the hematocrit of the erythrocyte concentrate obtained amounting to at least 50%,
  b) subjecting the first erythrocyte concentrate to plasma filtration, with the hematocrit increasing to at least 70%, and adding a second thrombocyte-containing plasma fraction to the first plasma fraction, and, optionally carrying out a third plasma filtration,
  c) mixing the erythrocyte concentrate obtained after the filtration with an additive solution, and
  d) freeing the whole blood or the erythrocyte concentrates of microaggregates and leukocytes by filtration.

The invention also provides a device for separating whole blood into an erythrocyte concentrate and plasma solution under gravitational force, the device including
  a first blood bag receiving whole blood,
  a plasma filter, which is divided into a blood chamber and a plasma chamber by a membrane that holds back erythrocytes and lets thrombocytes through, the blood chamber having a first connector and a second connector, and the plasma chamber having a further connector,
  a first tube line which extends from the first bag and is connected to the first connector of the blood chamber,
  a leukocyte filter which removes microaggregates and leukocytes,
  a second tube line which extends from the second connector of the blood chamber and is connected to a second blood bag,
  a third tube line which extends from the outlet of the plasma chamber and is connected to a plasma bag, and
  a first shut-off device for the first tube line, and a second shut-off device for the second tube line.

Further advantages of the invention will become clear from the description below.

The inventive method is employed on a whole-blood fraction which is to be treated either directly after it is taken from the donor, or after it has been stored for several hours. According to the stored embodiment, blood taken from a donor can be better treated in a leukocyte filter since, after storage for approximately 30 minutes or more, the degree of leukocyte separation is considerably better and thus satisfactory.

On the other hand, the separation of the leukocytes and other cells can be carried out immediately after withdrawal.

In the text below, such whole blood is designated as "stored" or "not stored."

According to a first embodiment, the leukocyte separation takes place immediately downstream of the bag containing the whole blood, and thus upstream of the plasma filter.

On the other hand, the location of this leukocyte separation is not critical and can also lie downstream of the filter, accordingly immediately upstream of the bag receiving the final erythrocyte concentrate (2nd embodiment). Finally, the leukocyte separation can also be performed upstream of the bag, that is to say in its supply line or transfer line (3rd embodiment).

The whole-blood fraction is thus passed through a filter which removes microaggregates and also leukocytes. Such filters are known for removing 99.9% and more of leukocytes from whole blood so that the whole blood is practically depleted of leukocytes.

In a further step, a whole blood thus depleted of leukocytes is separated by a plasma filter into a first erythrocyte concentrate and a first thrombocyte-containing plasma fraction via a microporous membrane which holds back the erythrocytes but allows all fluid components and thrombocytes to pass through. The plasma filter has been filled in advance with a saline solution which is separated as a precursor of the blood treatment.

In this separation step, the hematocrit, that is to say the volume share of erythrocytes in the whole blood, is increased to at least 45%–55%, preferably to at least 50%. As a consequence of this, depending on its provenance, ca. 10% to 20% by volume of the whole blood is usually removed as thrombocyte-containing plasma fraction at the plasma outlet of the plasma filter.

The plasma filtration in this step is effected by means of gravitational force, the hydrostatic pressure being a maximum of 1.5 m–2.5 m WC (0.15 bar–0.25 bar) between the outlet of the whole-blood bag and the inlet of the plasma filter, and may be carried out at a hydrostatic pressure of 1 m (0.1 bar) WC. The inlet pressure between blood bag and plasma filter is preferably at least 0.7 m, preferably approximately 1.5 m WC (water column) (corresponding to 0.07 bar–0.15 bar).

This relatively moderate pressure difference ensures that there is no hemolysis of the erythrocytes at the membrane.

The plasma filters employed usually have capillary membranes, that is to say hollow fiber membranes, and have a membrane surface of $0.1 \text{ m}^2$–$0.5 \text{ m}^2$.

Customary membrane materials are polymers of the EVA or PVA type, cellulose derivatives, polyolefins (polypropylene), PAN, PA, polyester, polysulfones and the like. Polysulfones or polypropylene are preferred.

A mean pore size of less than 2 μm, preferably between 1 μm and 1.5 μm, is chosen in order to separate thrombocytes (mean diameter approximately 0.5 μm–1 μm) from the remaining corpuscular components together with plasma.

To separate all cellular components from the plasma fraction, the customary pore sizes are between 0.03 and 0.4 μm depending on the membrane used in each case. The only important thing about the pore size is that the cellular constituents of the blood are held back by the membrane during the plasma filtration. Examples of filters that can be used are plasma filters sold by Dideco under the name "Hemaplex."

Such plasma filters are advantageously used already filled with a sterile, pyrogen-free saline solution and can thus be wetted with whole blood, particularly if they are made of a hydrophobic material.

Such filters have a housing which is divided by the semipermeable membrane into two chambers, namely a chamber guiding erythrocytes and other cells (leukocytes) with a first connector and a second connector, and a chamber guiding plasma, thrombocytes and plasma proteins with a plasma outlet.

At the second connector of the erythrocyte chamber (outlet according to the first erythrocyte enrichment), the erythrocyte concentrate enriched to at least 45%–55%, preferably 50% hematocrit, is collected in a first erythrocyte concentrate bag.

The bag for collecting the first erythrocyte concentrate is normally arranged slightly below the plasma filter, normally ca. 0.1 m–0.3 m, preferably up to 0.2 m WC.

In total, the pressure difference between the outlet of the whole-blood store and the inlet of the bag for the first erythrocyte concentrate is preferably between 1 m and 1.2 m WC.

The bag for collecting the cell-free plasma is likewise arranged below the filter in accordance with the law of gravity, normally up to 1 m WC, preferably between 0.75 m–0.9 m WC.

This total hydrostatic pressure of ca. 1.5 m–2.5 m, preferably 1.8 m–2 m WC, is sufficient for effective separation of plasma, without any danger of hemolysis.

To obtain the least possible amount of plasma in the final erythrocyte concentrate, the latter is subjected once again to plasma filtration with the same separation system, i.e. the same plasma filter is used, but with the reverse direction of flow through it, the same connector lines being used together with the same blood bag. As a result, the first erythrocyte concentrate flows out of the bag now arranged (gravimetrically speaking) above the plasma filter, the suspension height corresponding approximately to that of the whole-blood store, i.e. the hydrostatic pressure on the plasma filter corresponds to that of the first separation of whole blood. As a result, a second erythrocyte concentrate is collected at the first connector (inlet in the first step), and the hematocrit value of this erythrocyte concentrate is at least 60%, preferably 70%. By means of this second separation procedure, an erythrocyte concentrate is thus obtained in which approximately ⅔, preferably ¾ or more of the plasma originally present has been separated from the whole blood.

This second bag, like the first bag, is also gravimetrically arranged below the plasma filter at this second concentration, the height ratios corresponding to that of the first concentration of erythrocytes and the separation of the plasma.

This procedure can now be repeated once again until a hematocrit of 80%–90% is obtained and so that on the one hand the flowability of the blood is very considerably reduced and on the other hand ca. 15% of the original plasma remains in the erythrocyte concentrate. Since the residual amount of plasma is responsible for some of the side effects of the transfusion of erythrocyte concentrates, an advantage is here obtained which cannot be achieved to this extent by centrifugation.

To store an erythrocyte concentrate which has been obtained in this way, a substitute solution (additive solution) is advantageously provided in the second concentrate bag, as is customarily added to erythrocyte concentrates. These are aqueous solutions containing sodium chloride, adenine, glucose (SAG solution), if appropriate mixed with mannitol (SAG mannitol). Such solutions are, as has been established, known as additive systems for storage of erythrocyte concentrates.

According to the invention, the solution obtained in accordance with the second concentration step can be set to; a hematocrit equal to or greater than 70%.

The connection with additive solution then leads, for example, to a blood system with a normal hematocrit (40% and more).

After separation has taken place, the plasma bag according to a further embodiment is clamped off and is then available as cell-free plasma for freezing and storage. Moreover, the plasma chamber of the plasma filter can also be aerated under sterile conditions, which leads to emptying, so that a superior yield of approximately 50 ml of high-quality plasma is available. This yield is approximately 20% higher than in the customary centrifugation method.

After being clamped off, the erythrocyte bag contains residual plasma of approximately 15%. This erythrocyte concentrate has an additive solution added to it, as explained above, and is then thoroughly mixed. Thus, for example, it is possible to obtain a free-flowing product at a hematocrit of approximately 60%, which is available as an erythrocyte concentrate that has been depleted of leukocytes/thrombocytes/plasma.

In a further embodiment of the method according to the invention, erythrocyte concentrate still containing residual plasma can be washed with a saline solution, sterile saline solution first being added to the erythrocyte concentrate, which is then filtered again through the plasma filter. Thus, for example, 500 ml–1000 ml of 0.9% strength NaCl solution can be added to the erythrocyte concentrate after sterile connection, whereupon thorough mixing together takes place. Thereafter, the mixture obtained is conveyed through the plasma filter until a hematocrit of approximately 85% is again reached. The saline solution or a mixture containing this solution is collected in an empty bag. Additive solution is once again added, after which the product is available as an erythrocyte concentrate depleted in leukocytes/thrombocytes/plasma, i.e. the concentrate is washed substantially free of plasma according to this method step.

The method according to the invention can also be used to produce thrombocyte concentrates while at the same time recovering erythrocyte concentrates. For this purpose, a plasma filter is used with a membrane whose pore size (approximately 2 μm or smaller) is chosen such that it allows thrombocytes to pass through but holds back erythrocytes and leukocytes. After three filtration passes, it is again possible to obtain an erythrocyte concentrate with a hematocrit of approximately 85% and a plasma fraction rich in thrombocytes.

In a further embodiment, the plasma rich in thrombocytes can be further concentrated, this plasma being filtered through a conventional plasma filter (pore size max. 0.3 μm) which now holds back the thrombocytes. By repeated separation of, for example, 300 ml of starting plasma, it is possible then to produce 250 ml of cell-free plasma and approximately 15 ml of a plasma rich in thrombocytes.

Moreover, a conventional leukocyte depletion filter is used to remove the leukocytes from the erythrocyte concentrate obtained, with additive solution advantageously having been added to the concentrate to make it flowable.

The whole separation system is inherently sealed off in a sterile manner, so that a cell-free plasma product and an erythrocyte concentrate are produced which satisfy the quality requirements set for such products by the Paul Ehrlich Institute in Germany.

The inventive method may be carried out in the following way:

About half a liter of donor blood is either stored for at least half an hour in a blood bag or is passed through a filter directly after being obtained from the donor, said filter removing microaggregates and at least 99% of the leukocytes. This donor blood as whole blood is then subjected to the plasma separation according to the invention so as to produce an erythrocyte concentrate which at any rate contains ¼ of the original plasma.

According to a further embodiment (washing of the concentrate), the plasma content in the erythrocyte concentrate can be lowered to approximately 0.5% or less by washing with a wash solution, preferably a saline solution.

To be able to administer the stored blood to a patient in a manner ensuring the least possible risk of side effects (shivering, fever or shock), the erythrocyte concentrate obtained is first filtered free of leukocytes and microaggregates. As has been explained above, this is done either directly downstream or upstream of the stored whole blood, or before the inlet of the final erythrocyte concentrate bag.

The erythrocyte concentrate can be filtered free of thrombocytes upstream of the inlet of the final erythrocyte concentrate bag.

The treatment temperature corresponds approximately to room temperature. Whole blood is normally used at the temperature prevailing directly after the storage period. This can also lie between 23° C. and 35° C.

The hematocrit of the whole blood varies depending on its origin (man/woman) and is usually between 36% and 45%.

The running time within which the first plasma filtration takes place is dependent on the filtration pressure and the suction effect and is usually between 15 minutes and 45 minutes, advantageously about half an hour.

Hematocrit values of above 50%, advantageously above 52%–57%, are achieved after the first filtration.

After the first plasma separation, the bag containing the first erythrocyte concentrate and hanging below the plasma filter is suspended in a position which is above the plasma filter, so that by turning the bag the first erythrocyte concentrate flows back through the plasma filter in the reverse direction.

The second separation time is usually shorter than the first one and is approximately 15 minutes–40 minutes, usually 15 minutes–20 minutes.

In the second step, hematocrit values of between 65% and 75%, advantageously above 70%, in some cases above 73%, are obtained at the outlet of the plasma filter.

Moreover, a third filtration can also be performed which leads to the hematocrit being increased to ca. 80% or more.

An additive solution (SAG or SAG-M) is used to set the hematocrit of this second/third erythrocyte concentrate for its storage and also for its adjustment for a patient, the hematocrit set being approximately 40%–45%.

The materials used for the bags/lines are the polymers customarily used in medicine (PE, PP, etc.) which, on the one hand, are flexible and movable and, on the other hand, are easy to sterilize and optically transparent.

BRIEF DESCRIPTION OF THE DRAWINGS

The invention is illustrated with exemplary embodiments, with reference to drawing figures.

DETAILED DESCRIPTION OF THE DRAWINGS

Figure 1:
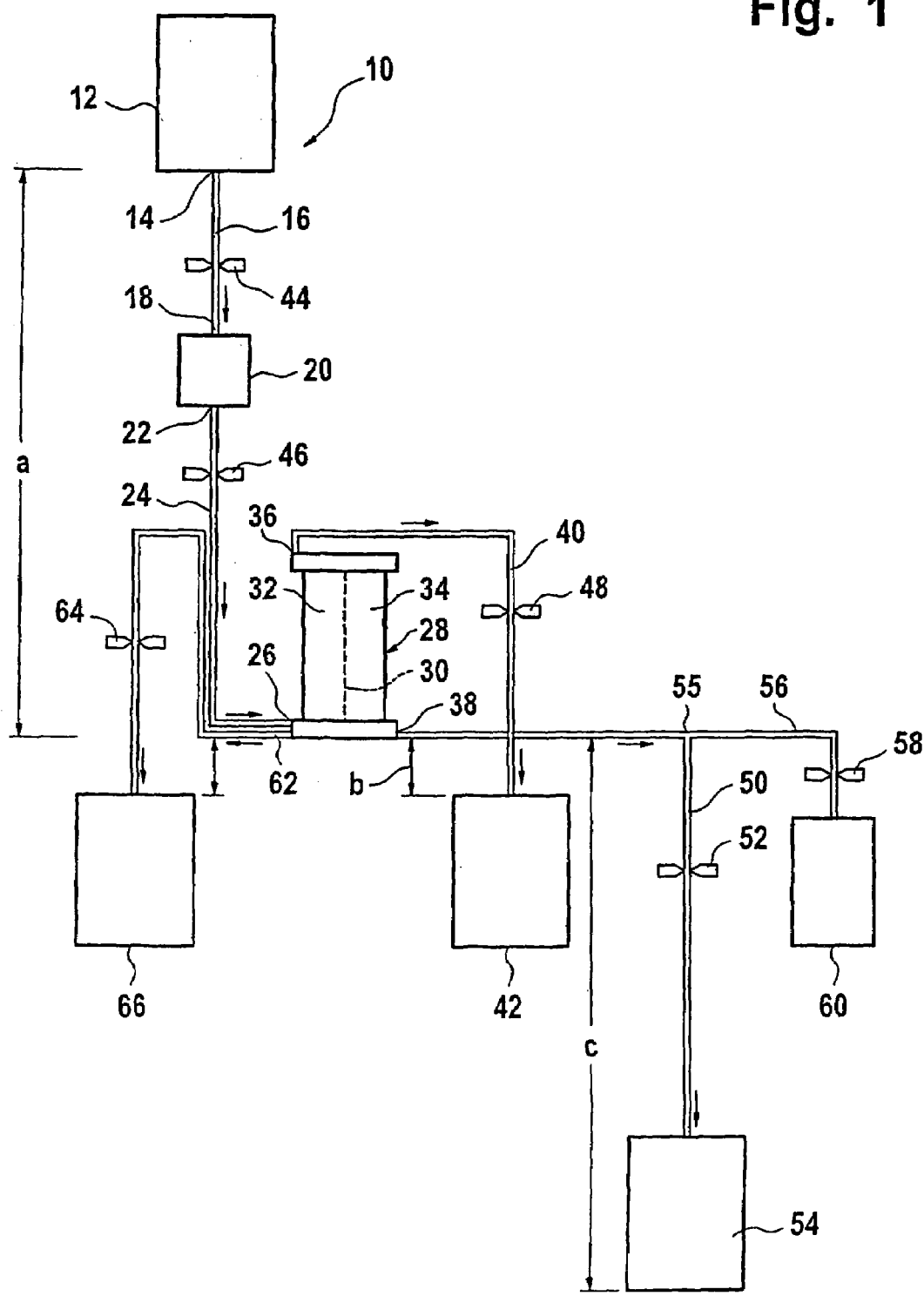
FIG. 1 shows a first diagrammatic structure of the plasma separation arrangement for producing the first erythrocyte concentrate according to a first embodiment.

In FIG. 1, reference numeral 10 designates a first embodiment of an arrangement for separating whole blood into plasma and erythrocyte concentrate. It comprises a whole-blood bag 12 which normally holds half a liter of whole blood.

An anticoagulant solution, for example an ACD or CBD solution, is added to this whole blood. These are conventional solutions based on glucose, trisodium citrate and citric acid, and they are provided in such a quantity that coagulation of blood does not take place within the separation system.

One end of a first flexible line 16 is connected to an outlet 14 of the whole-blood bag 10, another end 18 of the flexible line 16 being connected to a filter 20 which removes leukocytes and microaggregates. Extending from an outlet 22 of the filter 20 there is a second line 24 which is connected to a first connector 26 of a plasma filter 28. The plasma filter 28 is divided into a blood chamber 32 and a plasma chamber 34 by a membrane 30. Opposite the first connector 26, which opens into the blood chamber 32, there is a second connector 36 on the blood chamber, while a plasma connector 38 extends from the plasma chamber 34. Extending from the second connector 36 there is a third line 40 which is connected to a second blood bag 42 for receiving a first erythrocyte concentrate.

The respective lines 16, 24, and 40 have clamps 44, 46, and 48, respectively; with which the flexible lines can be opened and closed. The clamps are normally roller clamps.

Extending from the plasma connector 38 there is a fourth line 50, or plasma line, which can likewise be clamped off with a clamp 52. The end of the fourth line 50 opens into a plasma bag 54.

Upstream of the clamp 52, the fourth line 50 branches at a branch point 55 into a branch line 56 into which a clamp 58 is likewise coupled for clamping off the branch line. The branch line 56 itself is connected at its end to a collecting bag 60 which, as will be explained below, is intended to receive a filler solution for the plasma filter 28.

This branch line 56 does not necessarily have to branch off from the line 50. Instead, it can also be connected directly to the plasma connector 38.

Finally, a fifth line 62 issues from the first connector of the plasma filter 26, into which fifth line 62 a clamp 64 is likewise coupled. Another end of the fifth line 62 is connected to a third blood bag 66 which receives the second, final erythrocyte concentrate.

The third bag 66 already holds a prepared sterile blood-diluting solution as additive solution, for example an SAG solution.

In FIG. 1, the plasma filter 28 is arranged upright, i.e. the first connector 26 lies below the second connector 36, i.e. the flow is counter to the gravitational force when blood is conveyed from the connector 26 through the blood chamber 32 to the second connector 36, but on the other hand in the direction of the gravitational force when the direction of flow reverses, that is to say conveyed from connector 36 to connector 26.

As is clear from FIG. 1, the entire arrangement 10 is closed upon itself and is prefabricated in a sterile manner, i.e. it is sterile. An anticoagulant solution is present in the bag 12, a primer solution in the form of a saline solution in the plasma filter 28, and an additive solution in the third blood bag 66. All the clamps 44, 46, 48, 52, 58, and 64 are closed.

The arrangement 10 according to FIG. 1 is operated in the following way:

Whole blood is delivered to the whole-blood bag 12 via a blood-sampling line (not shown) and the bag is then sealed or welded. This whole blood is stored for at least 30 minutes in order to improve the separation of the leukocytes.

Following this, the clamps 44 and 46 are first opened so that the whole blood can flow through the filter 20. With the clamp 58 open, this whole blood enters the blood chamber 32 and initially displaces the saline solution through the pores of the membrane 30 into the plasma chamber 34. The hydrostatic pressure arising because of the distance a from the whole-blood bag 12 to the inlet 26 of the plasma filter 28 forces plasma through the pores of the membrane 30, with the clamp 58 open, and thus forces the primer solution out of the plasma connector 38 and through the line 50 to the branch 55, the line 56 and then into the collecting bag 60 whose dimensions are such that it can take up all of the primer solution. As soon as yellow-colored plasma appears at the branch 55, the clamp 58 is closed and the plasma clamp 52 is opened, so that plasma can run into the plasma bag 54. At the same time, the clamp 48 of the third line 40 is opened, so that erythrocyte concentrate can flow into the first erythrocyte concentrate bag.

The filtration proceeds until the whole-blood bag 12 is empty. Then, first erythrocyte concentrate is present in the second blood bag 42 arranged at a distance b below the plasma filter 28, while thrombocyte-containing plasma is present in the plasma bag 64 arranged at a distance c below the plasma filter 28.

Figure 2:
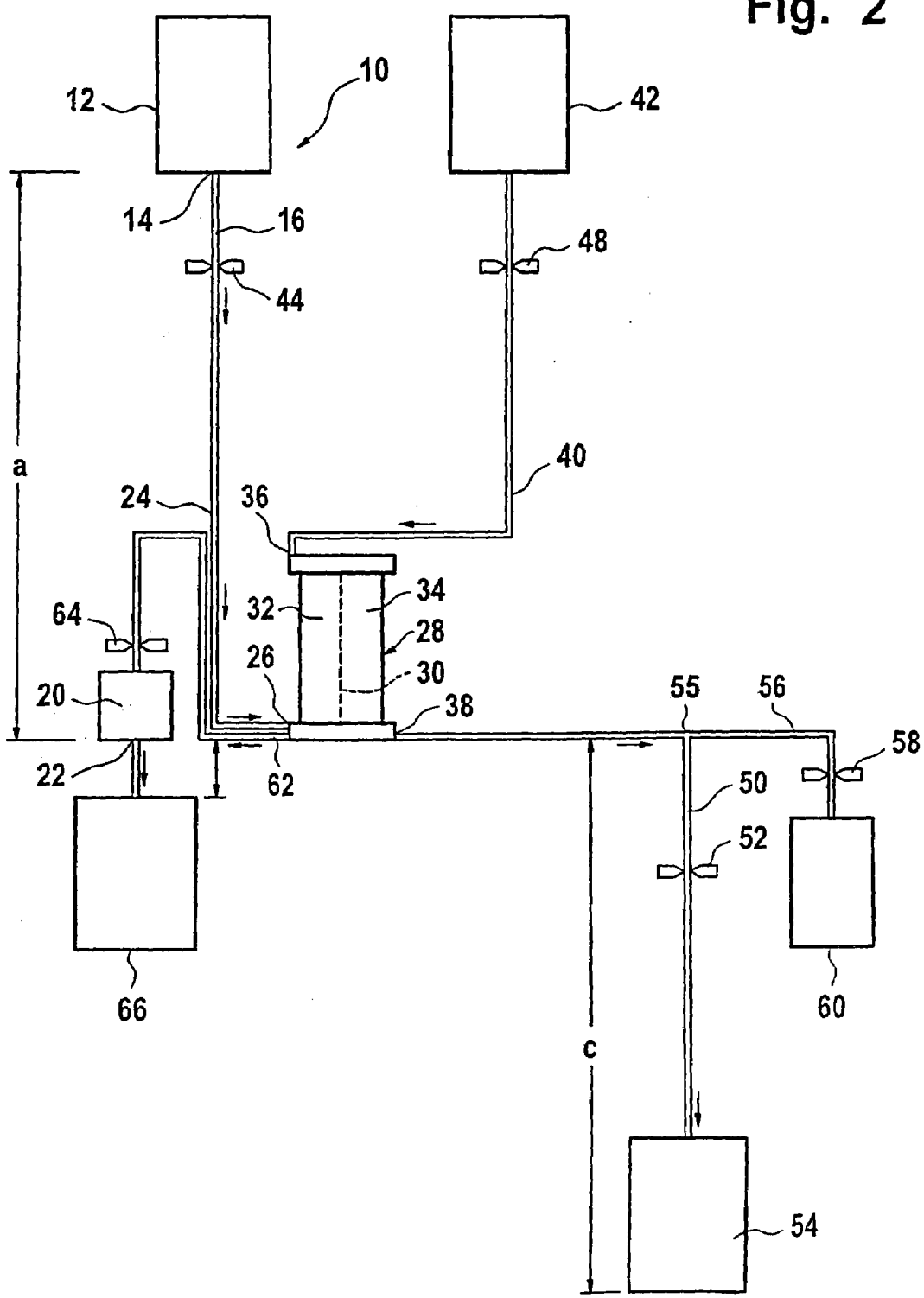
FIG. 2 shows a further diagrammatic structure of the arrangement according to FIG. 1 for producing the second erythrocyte concentrate.

In FIG. 2, the arrangement 10 is shown in the second separation step in which the second blood bag 42, which contains the first erythrocyte concentrate, is turned and brought into a position above the plasma filter 28, usually at the same distance a as the whole-blood bag 12 from the plasma filter 28.

FIG. 2 additionally shows a further embodiment of the arrangement of the leukocyte filter 20 which is not now arranged in the first line 16 but instead in the fourth line 62 downstream of the clamp 64.

Both arrangements of the leukocyte filter are equally feasible.

In the second separation step, the delivery line 16 is first closed with the aid of the clamp 46. At the same time, the fourth line 62 is opened with the aid of the clamp 64.

As can be seen from FIG. 2, the second erythrocyte bag n is situated below the plasma filter 28 by approximately the same distance b as the first erythrocyte bag 42 in the first separation step.

A plasma separation now takes place again in the opposite direction from the connector 36 to the connector 26 and from there through the line 62 into a bag 66.

As soon as the system has run empty, the plasma bag 54 and the bag 66 containing the second erythrocyte concentrate are welded shut and forwarded for further use. The rest is discarded.

In a further embodiment, the manually activated clamps can also be replaced by electrically operated clamps which are activated in a predetermined manner as has been explained above. A flow sensor is able to detect the end of the flow through the blood bags 12 and 42 in the second separation step. In this way, the subsequent operations, as explained above, can be triggered. At the end of the first separation procedure, the bag 42 can be brought from the lower position to the upper positions while at the same time the clamps are activated in the manner described above. As a result, the entire arrangement 10 can also be operated completely automatically.

Figure 3:
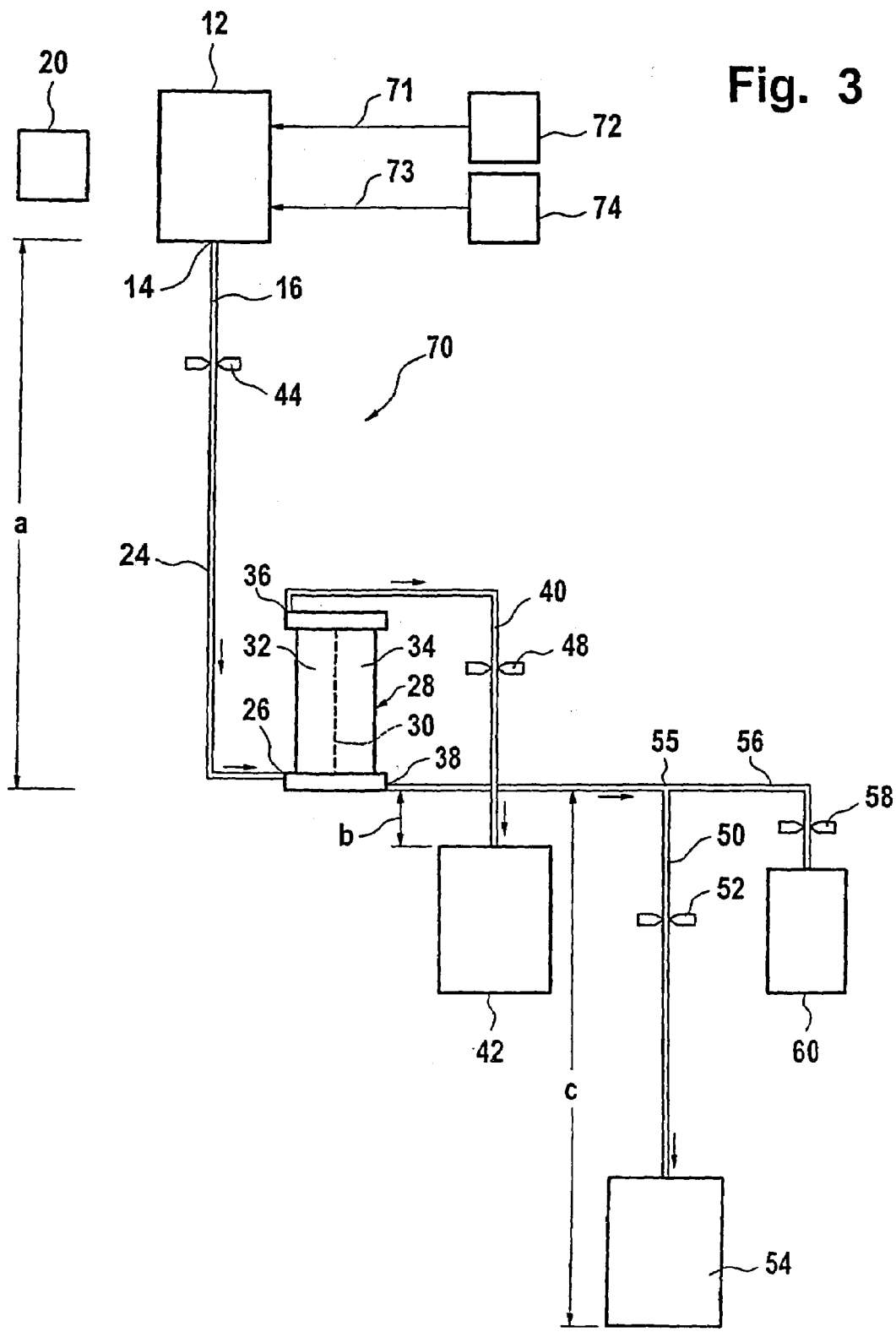
FIG. 3 shows a plasma separation arrangement similar to that in FIGS. 1 and 2, but without leukocyte filter in the supply line, according to a second embodiment.

FIG. 3 shows a further arrangement 70 for separating whole blood into plasma and erythrocyte concentrate as a further independent embodiment which largely corresponds to the arrangement 10, so that the reference numbers for the individual components have been retained. The arrangement 70 differs, however, essentially in that the filter 20 is no longer coupled into the line 16 but is instead located upstream of the whole-blood bag 12, which is represented symbolically in FIG. 3 by the fact that the filter 20 is not connected to the whole-blood bag 12. This therefore involves a filtration for removal of leukocytes that takes place outside the system. As a result, the clamp 46 and the arrangement of lines 62-66 are also not required, because the two bags 12 and 42 can be arranged alternately up or down. This state of affairs is illustrated in FIG. 4 which shows three filtration steps using two bags according to FIG. 3.

Figure 4:
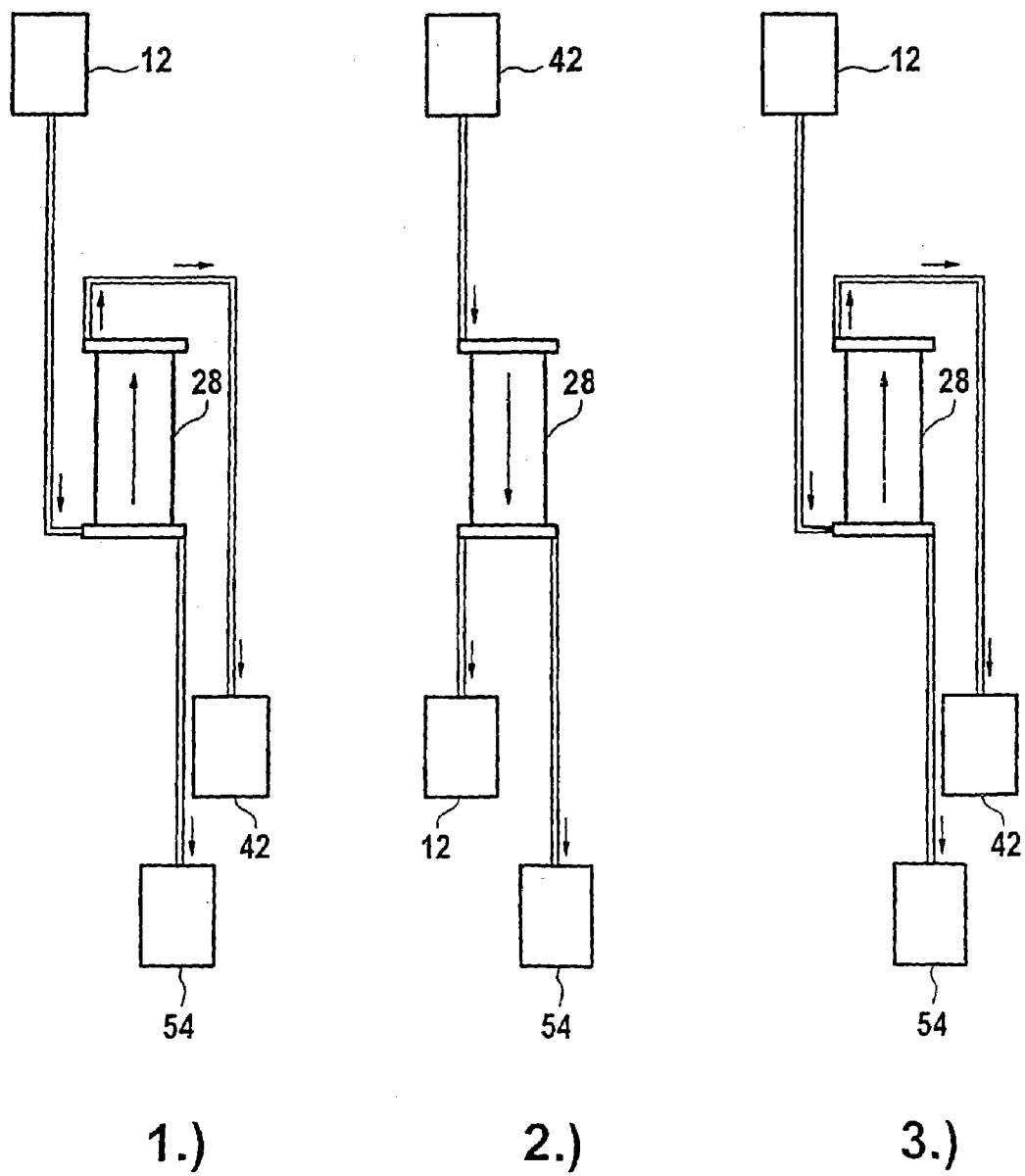
FIG. 4 shows a diagram of a 3-step plasma filtration using the arrangement according to FIG. 3.

FIG. 4 illustrates the individual filtration steps with raising or lowering of the bags 12 and 54, the direction of flow in the plasma filter 28 being indicated by an arrow.

Moreover, the arrangement 70 according to FIG. 3 can be provided with a bag 72 containing an additive solution. The bag 72 is connected to the whole-blood bag 12 via a closable line 71. At the end of the filtration procedure, therefore, the erythrocyte concentrate contained in the whole-blood bag 12 can be set to a predetermined hematocrit value with the additive solution.

Finally, in a further embodiment, a saline solution is provided in a further bag 74 which is connected to the whole-blood bag-via a line 73. This solution can be used to wash the erythrocyte concentrate in the whole-blood bag 12, by which means the plasma content can be lowered. As has already been described above, saline solution is fed into the whole-blood bag 12 via the line 73 and then mixed with the erythrocyte concentrate. Thereafter, renewed filtration under gravitational force takes place through the plasma filter 28. Additive solution, as has been described above, is then added to the concentrate.

EXAMPLE 552 g of whole blood (hematocrit 40.8%), which has been stored for 30 minutes after withdrawal from a donor, are subjected to plasma separation at 26° C. The whole blood is first passed through a leukocyte filter and freed of leukocytes outside the filtration system (cf. FIG. 3). Thereafter, the plasma separation is then conducted at temperatures of 32–26° C.

The running time is approximately 10±5 minutes, until the first separation is ended. A hematocrit of approximately 55–65% is achieved after the first separation step.

The distance a is up to 100 cm (=1 m WC). The distance b is 10 cm–20 cm, and c is 85 cm–100 cm.

The bags are then turned and the filtration direction reversed. The second phase thus begins. This is completed after 15±5 minutes. A hematocrit of approximately 65%–75% is achieved.

With a further pass, the hematocrit can be increased to 80–85. A net weight of the erythrocyte concentrate of ca. 180 g–200 g is achieved.

The invention claimed is:

1. A device for separating whole blood into an erythrocyte concentrate and thrombocyte-containing plasma under gravitational force, comprising
    a first blood bag receiving whole blood,
    a plasma filter, which is divided into a blood chamber and a plasma chamber by a membrane that holds back erythrocytes and lets thrombocytes through, the blood chamber having a first connector and a second connector, and the plasma chamber having a further connector,
    a first tube line which extends from the first blood bag and is connected to the first connector of the blood chamber,
    a leukocyte filter which removes microaggregates and leukocytes,
    a second tube line which extends from the second connector of the blood chamber and is connected to a second blood bag,
    a third tube line which extends from an outlet of the plasma chamber and is connected to a plasma bag,
    a fourth tube line which extends from the first connector of the blood chamber and is connected to a third blood bag, and
    a first shut-off device for the first tube line, and a second shut-off device for the second tube line, and a third shut-off device for the fourth tube line, wherein
    in a first step, the second blood bag is arranged gravimetrically below the plasma filter, and a first streaming path extends from the first blood bag through the blood chamber to the second blood bag with the first shut-off device and the second shut-off device being opened, and the third shut-off device being closed, and
    in a second step, a second streaming path extends from the second blood bag, which is arranged gravimetrically above the plasma filter, through the plasma filter to the third blood bag, with the first shut-off device being closed and the second shut-off device and the third shut-off device being opened, said second streaming path being in opposite direction to the first streaming path.

2. The device of claim 1, wherein the leukocyte filter is coupled into the first tube line, and a shut-off device is coupled into the first tube line downstream of the leukocyte filter.

3. The device of claim 1, wherein an outlet of the plasma filter is in fluidic communication with a collecting bag for a filler liquid of the plasma filter via a branch line, and a second clamp for shutting off the branch line and a clamp for shutting off the third tube line are provided.

4. The device of claim 1, wherein the third blood bag has an additive solution for mixing with the erythrocyte concentrate.

5. The device of claim 1, wherein the plasma filter has a mean pore size of 1 µ–2µ for filtering of plasma, proteins, and thrombocytes.

6. The device of claim 1, further comprising a thrombocyte filter with a mean pore size of 0.03 µ–0.4µ for filtering a thrombocyte concentrate from the thrombocyte-containing plasma.

* * * * *